US009903821B2

(12) United States Patent
Thalappil et al.

(10) Patent No.: US 9,903,821 B2
(45) Date of Patent: Feb. 27, 2018

(54) COATED MESOFLOWERS FOR MOLECULAR DETECTION AND SMART BARCODE MATERIALS

(71) Applicant: INDIAN INSTITUTE OF TECHNOLOGY MADRAS, Chennai, Tamil Nadu (IN)

(72) Inventors: Pradeep Thalappil, Chennai (IN); Sajanlal Panikkanvalappil Ravindranathan, Thrissur (IN)

(73) Assignee: INDIAN INSTITUTE OF TECHNOLOGY MADRAS, Chennai (IN)

( * ) Notice: Subject to any disclaimer, the term of this patent is extended or adjusted under 35 U.S.C. 154(b) by 154 days.

(21) Appl. No.: 14/888,193

(22) PCT Filed: Apr. 30, 2014

(86) PCT No.: PCT/IB2014/061096
§ 371 (c)(1),
(2) Date: Oct. 30, 2015

(87) PCT Pub. No.: WO2014/178006
PCT Pub. Date: Nov. 6, 2014

(65) Prior Publication Data
US 2016/0077010 A1  Mar. 17, 2016

(30) Foreign Application Priority Data

May 1, 2013 (IN) .......................... 1961/CHE/2013

(51) Int. Cl.
*B32B 5/16* (2006.01)
*C09C 1/00* (2006.01)
(Continued)

(52) U.S. Cl.
CPC ........... *G01N 21/658* (2013.01); *A61K 47/02* (2013.01); *B05D 5/061* (2013.01); *B05D 7/544* (2013.01);
(Continued)

(58) Field of Classification Search
CPC ... C09C 1/0006; C09C 1/0081; C09D 7/1225; C09D 7/1291; B82Y 30/00
(Continued)

(56) References Cited

U.S. PATENT DOCUMENTS 4,183,989 A  1/1980 Tooth
4,446,204 A  5/1984 Kaule et al.
(Continued)

FOREIGN PATENT DOCUMENTS

CN  1605024 A  4/2005
EP  0980763 A1  2/2000
(Continued)

OTHER PUBLICATIONS

Fales et al., Silica-coated gold nanostars for combined SERS detection and singlet oxygen generation: A potential nanoplatform for theranostics, Langmuir. 2011; 27(19): 12186-12190.*
(Continued)

*Primary Examiner* — Holly Le
(74) *Attorney, Agent, or Firm* — Maschoff Brennan

(57) ABSTRACT

Coated mesoflower are described including: a metallic mesoflower core having a first surface and including at least one protrusion terminating in a tip; a non-metallic coating covering and substantially conformal to the first surface, thereby creating an outer surface of the coated mesoflower; and a marker material having an optical property that is enhanced in the presence of the coated mesoflower. Coated hollow mesoflowers that do not have the metallic mesoflower core are also described.

18 Claims, 11 Drawing Sheets

(51) Int. Cl.
| | |
|---|---|
| G01N 21/65 | (2006.01) |
| C09D 7/12 | (2006.01) |
| G01N 21/64 | (2006.01) |
| A61K 47/02 | (2006.01) |
| B05D 5/06 | (2006.01) |
| B05D 7/00 | (2006.01) |
| B82Y 30/00 | (2011.01) |

(52) U.S. Cl.
CPC .......... *C09C 1/0006* (2013.01); *C09C 1/0081* (2013.01); *C09D 7/1225* (2013.01); *C09D 7/1291* (2013.01); *G01N 21/64* (2013.01); *B82Y 30/00* (2013.01)

(58) Field of Classification Search
USPC .................. 428/403, 323, 701; 977/781, 782
See application file for complete search history.

(56) References Cited

U.S. PATENT DOCUMENTS

| | | |
|---|---|---|
| 5,713,485 A | 2/1998 | Liff et al. |
| 5,853,464 A | 12/1998 | Macpherson et al. |
| 6,234,537 B1 | 5/2001 | Gutmann et al. |
| 6,255,948 B1 | 7/2001 | Wolpert et al. |
| 6,515,749 B2 | 2/2003 | Pipino |
| 6,610,351 B2 | 8/2003 | Shchegolikhin et al. |
| 6,686,074 B2 | 2/2004 | Muth et al. |
| 6,692,030 B1 | 2/2004 | Philips |
| 6,764,970 B1 | 7/2004 | Kuoni |
| 6,859,309 B2 | 2/2005 | Fischer, Jr. et al. |
| 7,288,320 B2 | 10/2007 | Steenblik et al. |
| 7,443,489 B2 | 10/2008 | Natan |
| 7,628,887 B2 | 12/2009 | Jääskeläinen et al. |
| 7,727,776 B2 | 6/2010 | Zhou et al. |
| 7,879,625 B1 | 2/2011 | Boss |
| 8,069,782 B2 | 12/2011 | Fragala et al. |
| 8,253,536 B2 | 8/2012 | Kaminska et al. |
| 2002/0021003 A1 | 2/2002 | McGrew |
| 2005/0277710 A1 | 12/2005 | Joyce et al. |
| 2007/0112784 A1 | 5/2007 | Blumenau |
| 2008/0118439 A1 | 5/2008 | Hancu et al. |
| 2008/0170230 A1 | 7/2008 | Gerion |
| 2008/0179405 A1 | 7/2008 | Benderly |
| 2009/0008925 A1 | 1/2009 | Blondiaux et al. |
| 2009/0140206 A1 | 6/2009 | Nie et al. |
| 2009/0220789 A1 | 9/2009 | DeSimone et al. |
| 2010/0195916 A1 | 8/2010 | Blondiaux et al. |
| 2010/0284917 A1 | 11/2010 | Kustner et al. |
| 2011/0043331 A1 | 2/2011 | Pradeep et al. |
| 2011/0049239 A1 | 3/2011 | Kukushkin et al. |

FOREIGN PATENT DOCUMENTS

| | | |
|---|---|---|
| JP | 2006247871 A | 9/2006 |
| WO | 2006086008 A2 | 8/2006 |
| WO | 2007031077 A1 | 3/2007 |
| WO | 2007149120 A2 | 12/2007 |
| WO | 2008010822 A2 | 1/2008 |
| WO | 2008030219 A2 | 3/2008 |
| WO | 2013144674 A2 | 10/2013 |
| WO | WO-2013/144674 A2 | 10/2013 |

OTHER PUBLICATIONS

Beija et al., Synthesis and applications of Rhodamine derivatives as fluorescent probes, Chem. Soc. Rev., 2009, 38, 2410-2433.*
"Fluorescence Detection of Counterfeit US Currency," JASCO, Inc. Molecular Spectroscopy, p. 26 (Feb. 2004).
Bailo, E., and Deckert, V., "Tip-enhanced Raman scattering," Chemical Society Review, vol. 37, pp. 921-930 (Mar. 31, 2008).
Clowers, B. H., et al., "Hadamard transform ion mobility spectrometry," Analytical Chemistry, vol. 78, Issue 1, pp. 44-51 (Jan. 1, 2006).
Cotte-Rodriguez, I., et al., "Desorption electrospray ionization of explosives on surfaces: Sensitivity and selectivity enhancement by reactive desorption electrospray ionization," Analytical Chemistry, vol. 77, Issue 21, pp. 6755-6764 (Nov. 1, 2005).
Dasary, S.S.R., et al., "Gold Nanoparticle Based Label-Free SERS Probe for Ultrasensitive and Selective Detection of Trinitrotoluene," Journal of the American Chemical Society, vol. 131, No. 38, pp. 13806-13812 (Sep. 8, 2009).
Fang, J., et al., "Gold Mesostructures with Tailored Surface Topography and Their Self-Assembly Arrays for Surface-Enhanced Raman Spectroscopy," NanoLetters, vol. 10, Issue 12, pp. 5006-5013 (Nov. 19, 2010).
Gunawidjaja, R., et al., "Bimetallic Nanocobs: Decorating Silver Nanowires with Gold Nanoparticles," Advance Materials, vol. 20, Issue 8, pp. 1544-1549 (Apr. 2, 2008).
International Search Report and Written Opinion for International Application No. PCT/IB14/61096 dated Feb. 20, 2015.
International Search Report and Written Opinion for International Application No. PCT/IB2010/002006, dated Feb. 4, 2011.
Larsson, A., et al., "A novel biochip technology for detection of explosives—TNT: Synthesis, characterisation and application," Sensors and Actuators B: Chemical, vol. 113, Issue 2, pp. 730-748 (Feb. 2006).
Leech, P. W. and Zeidler, H., "Microrelief structures for anti-counterfeiting applications," Microelectronic Engineering, vol. 65, Issue 4, pp. 439-446 (May 2003).
Li, J.F., et al., "Shell-isolated nanoparticle-enhanced Raman spectroscopy," Nature, vol. 464, pp. 392-395 (Mar. 18, 2010).
Liu, S., and Han, M.Y., "Silica-Coated Metal Nanoparticles," Chemistry—An Asian Journal, vol. 5, Issue 1, pp. 36-45 (Jan. 4, 2010).
Pinnaduwage, L. A., et al., "A sensitive, handheld vapor sensor based on microcantilevers," Review of Scientific Instruments, vol. 75, Issue 11, pp. 4554-4557 (Oct. 2004).
Prabakar, K., et al., "TiO2 thin film encapsulated ZnO nanorod and nanoflower dye sensitized solar cells," Materials Chemistry and Physics, vol. 125, Issue 1-2, pp. 12-14 (Jan. 1, 2011).
Sajanlal, P. R. and Pradeep, T., "Bimetallic Mesoflowers: Region-Specific Overgrowth and Substrate Dependent Surface-Enhanced Raman Scattering at Single Particle Level," Langmuir, vol. 26, Issue 11, pp. 8901-8907 (Feb. 23, 2010).
Sajanlal, P. R., "Functional Mesoflowers: A New Class of Materials for Molecular Sensing," Chennai Chemistry Confrence, pp. 1-8 (Feb. 17, 2011).
Sajanlal, P.R., et al., "Mesoflowers: A New Class of Highly Efficient Surface-Enhanced Raman Active and Infrared Absorbing Materials," Nano Research, vol. 2, Issue 4, pp. 306-320 (Apr. 2009).
Sajanlal, P.R., et al., "Wires, plates, flowers, needles, and core-shells: diverse nanostructures of gold using polyaniline templates," Langmuir, vol. 24, pp. 4607-4614 (Jun. 2008).
Spencer, K.M., et al., "Surface-enhanced Raman spectroscopy for homeland defense," Proceedings of SPIE, vol. 5269, p. 1, (Mar. 8, 2004).
Steinfeld, J. I., and Wormhoudt, J., "Explosives detection: a challenge for physical chemistry," Annual Review of Physical Chemistry, vol. 49, pp. 203-232 (1998).
Swagger, T.M., and Zheng, J., "Poly(arylene ethynylene)s in chemosensing and biosensing," Advances Polymer Science, vol. 177, pp. 151-179 (2005).
Xu, D., et al., "Development of chitosan-coated gold nanoflowers as SERS-active probes," Nanotechnology, vol. 21, No. 37, pp. 1-8 (Aug. 19, 2010).
Zhang, X., et al., "Rapid Detection of an Anthrax Biomarker by Surface-Enhanced Raman Spectroscopy," Journal of the American Chemical Society, vol. 127, Issue 12, pp. 4484-4489 (Mar. 8, 2005).
International Search Report and Written Opinion in International Application No. PCT/IB2014/061096 dated Feb. 20, 2015. (26 pages).
Liu, S. and Han, M., "Silica-Coated Metal Nanoparticles," Chemistry—An Asian Journal, vol. 5, Issue 1, pp. 36-45. (2010).

\* cited by examiner

COATED MESOFLOWERS FOR MOLECULAR DETECTION AND SMART BARCODE MATERIALS

CROSS-REFERENCE TO RELATED APPLICATIONS

This application is a U.S. National Stage Application under 35 U.S.C. § 371 of International Application No. PCT/IB2014/061096, filed Apr. 30, 2014, which claims priority under 35 U.S.C. §119(a) from India Patent Application Ser. No. 1961/CHE/2013, filed May 1, 2013, entitled "COATED MESOFLOWERS FOR MOLECULAR DETECTION AND SMART BARCODE MATERIALS", the contents of which are incorporated herein in their entirety.

BACKGROUND

Raman scattering in a molecule occurs when light impinges upon the molecule and interacts with the electron cloud and the bonds of that molecule. For the spontaneous Raman effect, which is a form of light scattering, a photon excites the molecule from the ground state to a virtual energy state. When the molecule relaxes it emits a photon and it returns to a different rotational or vibrational state. The difference in energy between the original state and this new state leads to a shift in the emitted photon's frequency away from the excitation wavelength. The Raman effect, which is a light scattering phenomenon, should not be confused with absorption (as with fluorescence) where the molecule is excited to a discrete (not virtual) energy level.

If the final vibrational state of the molecule is more energetic than the initial state, then the emitted photon will be shifted to a lower frequency in order for the total energy of the system to remain balanced. This shift in frequency is designated as a Stokes shift. If the final vibrational state is less energetic than the initial state, then the emitted photon will be shifted to a higher frequency, and this is designated as an Anti-Stokes shift. Raman scattering is an example of inelastic scattering because of the energy transfer between the photons and the molecules during their interaction.

Raman spectroscopy is a spectroscopic technique used to study vibrational, rotational, and other low-frequency modes in a system, such as a molecule. It relies on inelastic scattering, also know as Raman scattering, of monochromatic light, for example from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system.

Raman spectroscopy is commonly used in chemistry, since vibrational information is often specific to the chemical bonds and symmetry of molecules. Therefore, the Raman spectrum of a molecule (that is, a measure of Raman scattering as a function of wavelength of light incident on the molecule) provides a fingerprint by which the molecule can be detected and identified.

Surface enhanced Raman scattering (SERS) is a surface-sensitive technique that enhances Raman scattering by molecules adsorbed on a surface. The enhancement factor can be significant (for example, a factor on the order of $10^7$ or more). This enhancement may increase the available signal strength for Raman spectroscopy, allowing for molecular detection and identification when only a small sample is available. In some cases, SERS enhancement allows for detection on the single molecule level.

Tip enhanced Raman scattering (TERS) refers to SERS type enhanced scatter effect for molecules adsorbed on a portion of a surface formed as a tip (typically having a size of about 1 nm to about 100 nm). In some cases TERS provides increased scattering enhancement due, for example, to localized electric field effects in the vicinity of the tip.

SUMMARY

The present disclosure described embodiments of a coated mesoflower material. In some embodiments, the mesoflower material can enhance an optical property (for example, Raman scattering strength) of a material or analyte adsorbed on the surface of the mesoflower. Embodiments of the coated mesoflowers have a wide range of applications including chemical detection, biosensing, material tagging, smart barcode applications, medical applications, and more.

In one aspect, a coated mesoflower is disclosed including: a metallic mesoflower core having a first surface and including at least one protrusion terminating in a tip; a non-metallic coating covering and substantially conformal to the first surface, thereby creating an outer surface of the coated mesoflower; and a marker material having an optical property that is enhanced in the presence of the coated mesoflower.

In another aspect, a detector for detecting the presence of an analyte is disclosed, the detector including a plurality of coated mesoflower. Each coated mesoflower includes a metallic mesoflower core having a first surface and including at least one protrusion terminating in a tip; a non-metallic coating covering and substantially conformal to the first surface, thereby creating an outer surface of the coated mesoflower; and a marker material having an optical property. The detector further includes a sensor configured to detect one or both of an optical property of the analyte and an optical property of the marker material in the presence of the analyte. In some embodiments, the optical property of the analyte and the optical property of the marker material are greater in the presence of the coated mesoflowers than in the absence of the coated mesoflowers.

In another aspect, an apparatus is disclosed for determining the information related to a substance, the substance having been treated to include a plurality of coated mesoflowers. Each coated mesoflower includes: a metallic mesoflower core having a first surface and including at least one protrusion terminating in a tip; a non-metallic coating covering and substantially conformal to the first surface, thereby creating an outer surface of the coated mesoflower; and a marker material having an optical property that is enhanced in the presence of the coated mesoflower. The apparatus includes: a sensor for detecting marker information related to the enhanced optical property of the marker material; and a processor configured to determine the information related to a substance based on the detected marker information.

In another aspect, a method of characterizing a substance is disclosed, the method including: providing the substance; contacting the substance and multiple coated mesoflowers, each coated mesoflower including: a metallic mesoflower core having a first surface and including at least one protrusion terminating in a tip; a non-metallic coating covering and substantially conformal to the first surface, thereby creating an outer surface of the coated mesoflower; and a marker material having an optical property that is enhanced in the presence of the coated mesoflower. The method further includes: detecting an optical property of the substance. In some embodiments, the optical property of the substance in the presence of the coated mesoflowers is greater than the optical property of the substance in the absence of the coated mesoflowers.

In another aspect, a method of making a coated mesoflower including: obtaining a metallic mesoflower core having a first surface and including at least one protrusion terminating in a tip; forming a non-metallic coating covering and substantially conformal to the first surface, thereby creating an outer surface of the coated mesoflower; and applying a marker material to the non-metallic coating, the marker material having an optical property that is enhanced in the presence of the coated mesoflower.

In another aspect, a method of delivering a therapeutic agent to a treatment area in a subject is disclosed, the method including: obtaining a plurality of coated mesoflowers, each coated mesoflower including: a metallic mesoflower core having a first surface and including at least one protrusion terminating in a tip; and a non-metallic coating covering and substantially conformal to the first surface, thereby creating an outer surface of the coated mesoflower, where the non-metallic coating includes at least one cavity and the cavity contains the therapeutic agent; and delivering the plurality of coated mesoflowers to the treatment area.

In another aspect, a method of delivering a therapeutic heat to a treatment area in a subject is disclosed, the method including: obtaining a plurality of coated mesoflowers, each coated mesoflower including: a metallic mesoflower core having a first surface and including at least one protrusion terminating in a tip; and a non-metallic coating covering and substantially conformal to the first surface, thereby creating an outer surface of the coated mesoflower. The method includes delivering the plurality of coated mesoflowers to the treatment area; and applying near infrared light to the treatment area to heat the coated mesoflowers.

In another aspect, a coated hollow mesoflower includes: a hollow mesoflower core having a first surface, and including at least one protrusion terminating in a tip; a non-metallic coating covering and substantially conformal to the first surface, thereby creating an outer surface of the coated hollow mesoflower; and a marker material having an optical property, and at least partially embedded in the non-metallic coating.

In another aspect, a method of making a coated hollow mesoflower includes: obtaining a metallic mesoflower core having a first surface, and including at least one protrusion terminating in a tip; forming a non-metallic coating covering and substantially conformal to the first surface to form a coated mesoflower; removing the metallic mesoflower core from the coated mesoflower to form a hollow mesoflower core covered by the non-metallic coating; and at least partially embedding a marker material having an optical property in the non-metallic coating.

In another aspect, a tag includes: at least one coated hollow mesoflower including: a hollow mesoflower core having a first surface, and including at least one protrusion terminating in a tip; a non-metallic coating covering and substantially conformal to the first surface, thereby creating an outer surface of the coated hollow mesoflower; and a marker material having an optical property, and at least partially embedded in the non-metallic coating, wherein the optical property is substantially undetectable under a first condition and is detectable under a second condition different from the first condition.

In another aspect, a method of using a tag includes: exposing the tag to at least one condition, the tag including: at least one coated hollow mesoflower including: a hollow mesoflower core having a first surface, and including at least one protrusion terminating in a tip; a non-metallic coating covering and substantially conformal to the first surface, thereby creating an outer surface of the coated hollow mesoflower; and a marker material having an optical property, and at least partially embedded in the non-metallic coating, wherein the at least one condition reveals the optical property of the marker material.

In another aspect, a detector for detecting the presence of an analyte includes: a plurality of coated hollow mesoflowers, each coated hollow mesoflower including: a hollow mesoflower core having a first surface and comprising at least one protrusion terminating in a tip; a non-metallic coating covering and substantially conformal to the first surface, thereby creating an outer surface of the coated hollow mesoflower; and a marker material having an optical property; and a sensor configured to detect an optical property of the marker material in the presence of the analyte; wherein the optical property of the marker material is greater in the presence of the coated mesoflowers than in the absence of the coated mesoflowers.

In another aspect, a method of detecting the presence of an analyte includes: contacting the analyte with a plurality of coated hollow mesoflowers, each coated hollow mesoflower including: a hollow mesoflower core having a first surface, and comprising at least one protrusion terminating in a tip; a non-metallic coating covering and substantially conformal to the first surface, thereby creating an outer surface of the coated hollow mesoflower; and a marker material having an optical property; and detecting the optical property of the marker material in the presence of the analyte; wherein the optical property of the marker material is greater in the presence of the coated mesoflowers than in the absence of the coated mesoflowers.

In another aspect, a method of delivering a therapeutic agent to a treatment area in a subject includes: obtaining a plurality of coated hollow mesoflowers, each coated hollow mesoflower including: a hollow mesoflower core having a first surface, and comprising at least one protrusion terminating in a tip; a non-metallic coating covering and substantially conformal to the first surface, thereby creating an outer surface of the coated hollow mesoflower, wherein the non-metallic coating comprises at least one cavity, and one or both of the hollow mesoflower core and the cavity contain the therapeutic agent; and delivering the plurality of coated hollow mesoflowers to the treatment area.

In another aspect, an anti-reflective coating includes: coated hollow mesoflowers, each coated hollow mesoflower including: a hollow mesoflower core having a first surface, and including at least one protrusion terminating in a tip; and a non-metallic coating covering and substantially conformal to the first surface, thereby creating an outer surface of the coated hollow mesoflower.

Various embodiments may include any of the above-described features, either alone, or in any suitable combination.

As will be familiar to one skilled in the art, throughout this disclosure a core-shell structure may be referred to using the nomenclature X@Y where X is the core material and Y is the shell material. This nomenclature may be extended to multiple shell structures. For example X@Y@Z would refer to a core of material X surrounded by a shell of material Y that is, in turn, surrounded by a shell of material Z.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the disclosed technology and together with the description serve to explain principles of the disclosed technology.

DETAILED DESCRIPTION

Coated Mesoflowers

Figure 1:
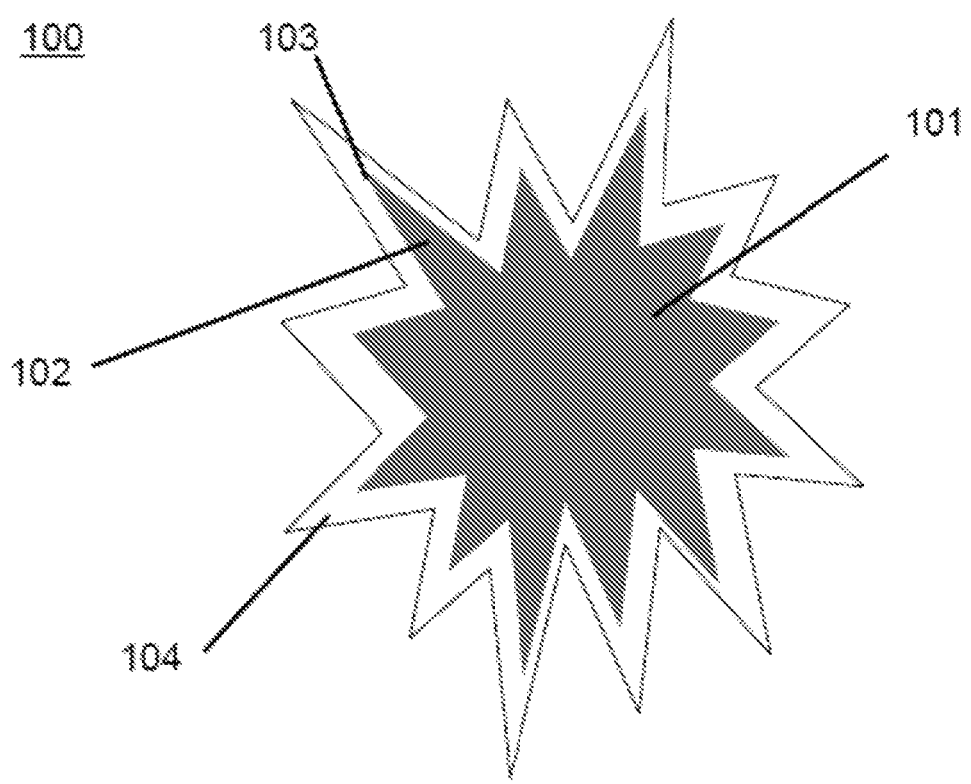
FIG. 1 is an illustration of a coated mesoflower.

Referring to FIG. 1, a coated mesoflower 100 includes a metallic mesoflower core 101 having a surface that includes protrusions 102 (also referred to herein as "stems") each terminating in a tip 103. The metallic mesoflower core 101 may have a largest dimension of about 100 nm to about 10 μm. The size of the protrusions 102 may be about 1 nm to about 500 nm.

In some embodiments, the coated mesoflower 100 is made up of a spiky stems projecting from a central core in all directions. In some embodiments, the coated mesoflower 100 has a characteristic morphology, for example, resembling a natural object (for example, a starfish, and aloe vera plant, or a pineapple).

The metallic mesoflower core 101 can be made of one or more metals including, for example, gold (Au), silver (Ag), or combinations thereof. In some embodiments, the metallic mesoflower core 101 may be replaced with a mesoflower core made of a non-metallic, but electrically conductive material, for example, a highly doped semiconductor material.

In some embodiments, the metallic mesoflower core 101 includes a core of a first metallic material and a shell of a second metallic material different from the first metallic material. As noted above, throughout this disclosure a core-shell structure may be referred to using the nomenclature X@Y where X is the core material and Y is the shell material. This nomenclature may be extended to multiple shell structures. For example X@Y@Z would refer to a core of material X surrounded by a shell of material Y that is, in turn, surrounded by a shell of material Z. In some embodiments, the metallic mesoflower core 101 has the structure, X@Y, where X is a first metal and Y is a second metal different from the first metal. In some embodiments, the first and second metals are noble metals. For example, in some embodiments, the metallic mesoflower core 101 has the structure Au@Ag.

A non-metallic coating 104 covers and may be substantially conformal to the metallic mesoflower core 101, thereby creating an outer surface of the coated mesoflower 100. The non-metallic coating may include an oxide, such as a silicon oxide, a metal oxide, or combinations thereof. In various embodiments any suitable oxide may be used including alumina, titania, silica, zirconia, and combinations thereof. The non-metallic coating 104 may have one or more marker materials at least partially or entirely embedded in the non-metallic coating 104, as will be described in the section "Coated Mesoflowers with Embedded Markers".

The non-metallic coating 104 may have any suitable thickness, for example, about 1 nm to about 500 nm, or any subrange thereof. In some embodiments, the non-metallic coating has a thickness of about 2 nm to about 500 nm, for example, about 2 nm, about 50 nm, about 100 nm, about 150 nm, about 200 nm, about 250 nm, about 300 nm, about 350 nm, about 400 nm, about 450 nm, about 500 nm, or a thickness between any two of these values.

In some embodiments, the non-metallic coating 104 protects the metallic mesoflower core 101, for example, from physical and/or thermal damage. For example, in some embodiments, in the presence of the coating 104, the morphology of the metallic mesoflower core may remain stable at higher temperatures than would be the case for an equivalent bare metallic mesoflower core. For example, in some embodiments, the coated mesoflower 100 may be thermally stable at temperatures greater than about 400 degrees Celsius, about 500 degrees Celsius, or about 600 degrees Celsius. In some embodiments, the coated mesoflower is characterized as being thermally stable at temperatures of about 0 degrees Celsius to about 1000 degrees Celsius, or any subrange thereof.

In some embodiments, the non-metallic coating 104 may include one or more cavities, channels, or other features (not shown). For example, in some embodiments cavities or channels may be formed in the vicinity of the tips 103 in the space between the metallic mesoflower core 101 and the non-metallic coating 101. In some embodiments, these cavities or channels may be filled with one or more materials (for example, a drug or therapeutic agent, as discussed below).

In some embodiments, the coated mesoflower 100 is capable of enhancing an optical property of at least one material or analyte in the presence of the coated mesoflower, for example, adsorbed on the outer surface of the coated mesoflower 100. In some embodiments the optical property is Raman scattering, which may be enhanced by of factor of at least $10^6$, $10^7$, $10^8$, or more, for example, about $10^6$ to about $10^{11}$, or any subrange thereof. In some embodiments, for example, where the material is adsorbed on the surface of the coated mesoflower 100, the Raman scattering is enhanced via a SERS process. In some embodiments, for example, where the material is adsorbed on the surface of the coated mesoflower 100 in the vicinity of the tips 103, the Raman scattering is enhanced via a TERS process.

In some embodiments, the enhancement provided by the coated mesoflower 100 may be greater than the enhancement that would be provided by a corresponding bare metallic mesoflower, for example, by a factor of 10, 100, 1000, or more. In some embodiments, the increased enhancement exhibited in the presence of the coated mesoflower 100 may be due, at least in part, to the fact that the non-metallic coating 104 maintains a physical and/or electrical separation between the adsorbed material and the surface of the metallic mesoflower core 101.

In some embodiments an optical property other than Raman scattering may be enhanced by the coated mesoflowers 100, including: color, absorption properties, transmission properties, fluorescence, or combinations thereof.

In some embodiments, the outer surface of the coated mesoflower 100 may be, functionalized, for example, to promote adsorption of a selected target material.

The coated mesoflowers, and various embodiments of the coated mesoflowers including the coated mesoflowers with embedded markers and the coated hollow mesoflowers as will be described below, may selectively absorb light in a desired wavelength range. The anisotropic nature of the coated mesoflowers and their various embodiments, allows them to absorb light having wavelengths ranging from the visible region to the IR region. The absorption spectra of the coated mesoflowers and various embodiments thereof, can be dependent on size of the coated mesoflowers, and thickness of layers formed by the coated mesoflowers and various embodiments thereof. In some embodiments, the coated mesoflowers and various embodiments of the coated mesoflowers, may selectively absorb light in the wavelength range of about 400 nm to about 2000 nm, or any subrange thereof. In some embodiments, the coated mesoflowers may selectively absorb light in the wavelength range of about 700 nm to about 2000 nm, or any subrange thereof.

Analyte Detection Using Coated Mesoflowers

In some embodiments, coated mesoflowers 100, of the type described above, may be used in the detection and/or identification of an analyte or a target material. The mesoflowers act to enhance a measured optical property of the target material, thereby aiding in the detection. In some embodiments, the optical property of the analyte is Raman scattering. The coated mesoflowers may have one or more marker materials at least partially embedded in the non-metal coating. The marker material can exhibit an optical property in the presence of the analyte, and that optical property can be enhanced in the presence of the mesoflowers. In some embodiments, the optical property of the marker material is Raman scattering, fluorescence or both.

Figure 2:
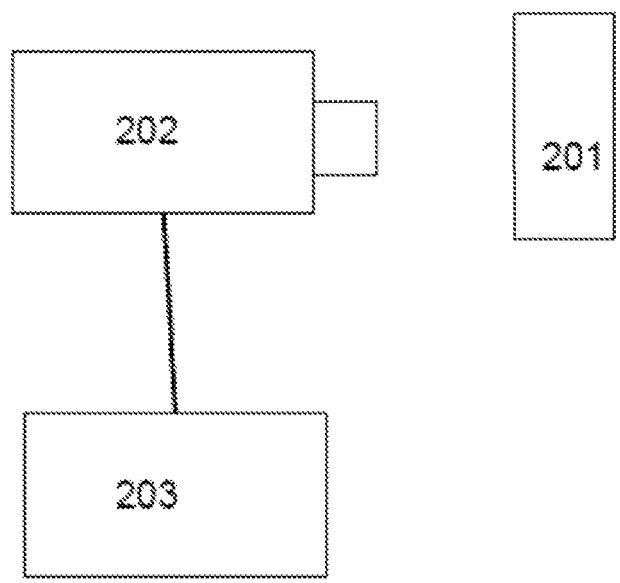
FIG. 2 is a schematic of a detector for detecting an analyte having an optical property enhanced by coated mesoflowers.

FIG. 2 shows an embodiment of a detector 200 for detecting a target material using the coated mesoflowers 100. A sample 201 includes an analyte and the coated mesoflowers 100. For example, in one embodiment, the sample 201 includes a glass slide on which a powder of the coated mesoflowers 100 has been applied. A solution of analyte is applied to the slide (for example, by drip casting), such that analyte present in the solution would become adsorbed on the surface of the mesoflowers 100.

A sensor 202 detects an optical property of the sample and/or the marker material and a processor 203 processes the detected optical property to determine the presence and/or identity of a target material in the sample. In some embodiments, the sensor 202 detects one or both of the optical property of the analyte and the optical property of the marker material. The coated mesoflowers 100 are selected such that, if the target material is present in the sample, an optical property of the sample and/or the marker material measured by the sensor 202 is enhanced. In some embodiments, this allows for detection of the target material even only present in small amounts and/or low concentration in the sample. Some embodiments allow detection of the target material down to the molecular level (that is, such that the presence of a few molecules, or even a single molecule may be detected).

In some embodiments, the detector may be a Raman spectroscopy detector that obtains a Raman spectrum of the sample 201. The coated mesoflowers 100 are selected to enhance Raman scattering by the target material. The processor 203 identifies the target material in the sample by identifying characteristic features in the measured spectrum.

In some embodiments, the detector 100 may include a light source (not shown), for illuminating the sample 201. In some embodiments, the light source may be used to illuminate the sample 201 with light having a selected wavelength or range of wavelengths. In some embodiments, the source may illuminate the sample at selected wavelengths ranging from the ultraviolet to the infrared. For example, in some embodiments, the wavelength of the source may be tuned to a wavelength of about 400 nm to about 2000 nm, or any subrange thereof.

In some embodiments, the source is a wavelength tunable source, such as a wavelength tunable laser or light emitting diode (LED). In some embodiments, the source may include a broadband source and one or more optical elements (for example a filter, a monochromer, a diffraction grating, and so on) use to control the wavelength of light delivered to the sample 201.

Various other embodiments of detector 200 may be used. For example, in some embodiments, the detector may be configured to detect the presence of the analyte in a gas or liquid sample in which coated mesoflowers 100 have been dispersed. In some embodiments an optical property other than a Raman spectrum may be measured by the sensor 202, including: a color, an absorption spectrum, a transmission spectrum, fluorescence, or combinations thereof.

In some embodiments, the detector 200 may be an integrated unit, for example, a lab-on-a-chip device. In some embodiments, multiple detectors 200 may be used, for example, to process a number of samples in parallel.

Coated Mesoflowers with Embedded Markers

Figure 3:
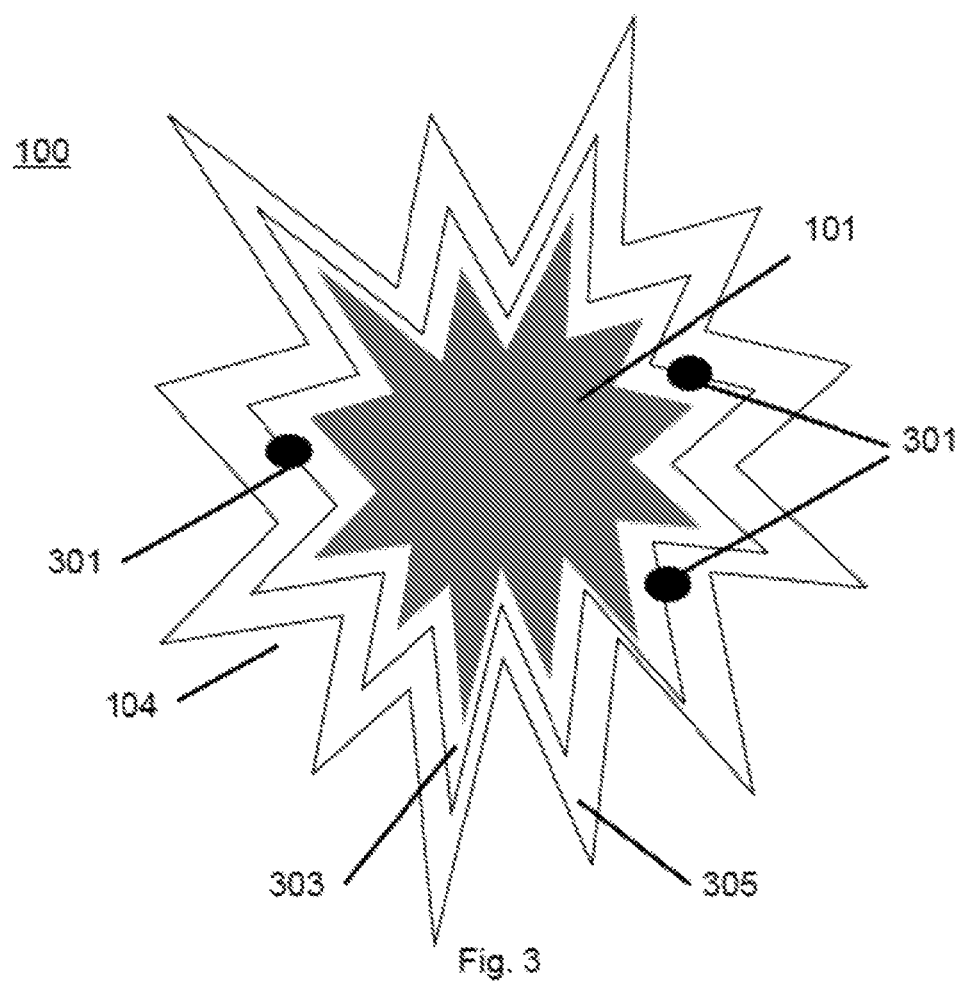
FIG. 3 is an illustration of a coated mesoflower with an embedded marker material.

FIG. 3 shows an embodiment of the coated mesoflower 100 of FIG. 1 (including a metallic mesoflower core 101 surrounded by a non-metallic coating 104) further including a marker material 301 having an optical property that is enhanced in the presence of the coated mesoflower 100. For example, the marker material may be a material having a Raman spectrum enhanced by the coated mesoflower 100 (for example, by a SERS or TERS process). The marker material may alternatively be a material having a fluorescence enhanced by the coated mesoflower 100. Therefore, in some embodiments, the marker material is a Raman active material, a fluorescent material, or both. The Raman active material, in some embodiments, includes surface enhanced Raman scattering (SERS) active molecules. The SERS active molecules can for example include crystal violet, rhodamine 6G, methylene blue, or any combination thereof. In some embodiments, the fluorescent material includes organic molecules, for example, rhodamine 6G, fluorescein isothiocyanate, or any combination thereof. Other than organic molecules, the fluorescent material, may include the semiconductor quantum dot, rare-earth nanocrystal, metallic quantum cluster, or any combination thereof. The optical property may be used to identify the marker material 301. For example, the Raman spectra of the marker material 301 may be used as a "fingerprint" that may be used to identify the marker material 301, for example, using spectroscopic techniques.

As shown, in some embodiments, the marker material 301 is at least partially embedded in the non-metallic coating 104. In some embodiments the marker material 301 is embedded in the non-metallic coating 104 such that the marker material 301 does not contact the first surface of the metallic mesoflower core 101. In some embodiments, this separation may serve to increase the enhancement of the enhanced optical property of the marker material 301.

As shown, in some embodiments, the non-metallic coating 104 includes a first layer 303 including the marker material 301, and an overlayer 305 covering the first layer 303. The overlayer 305 may protect and/or inhibit removal of the marker material 301.

Coated mesoflowers including marker materials of the type described above may be used in a variety of applications where it would be desirable to identify, track, or otherwise provide information about a substance. The coated mesoflowers may be combined with the substance (for example, mixed with the substance, applied to the substance, embedded in the substance, and so on). In some embodiments, the morphology of the mesoflowers may act to securely attach the mesoflowers to the substance and/or inhibit or prevent the removal of the mesoflowers from the substance.

A characteristic optical property of the marker (for example, one or more features in the Raman spectrum of the marker material) may be associated with information related to the substance, including, for example, information related to a chemical property of the substance, information related to a production source of the substance, information identifying a production batch of the substance, information related to ingredients of the substance, information related to the recyclability of the substance, or any other suitable information.

Figure 4:
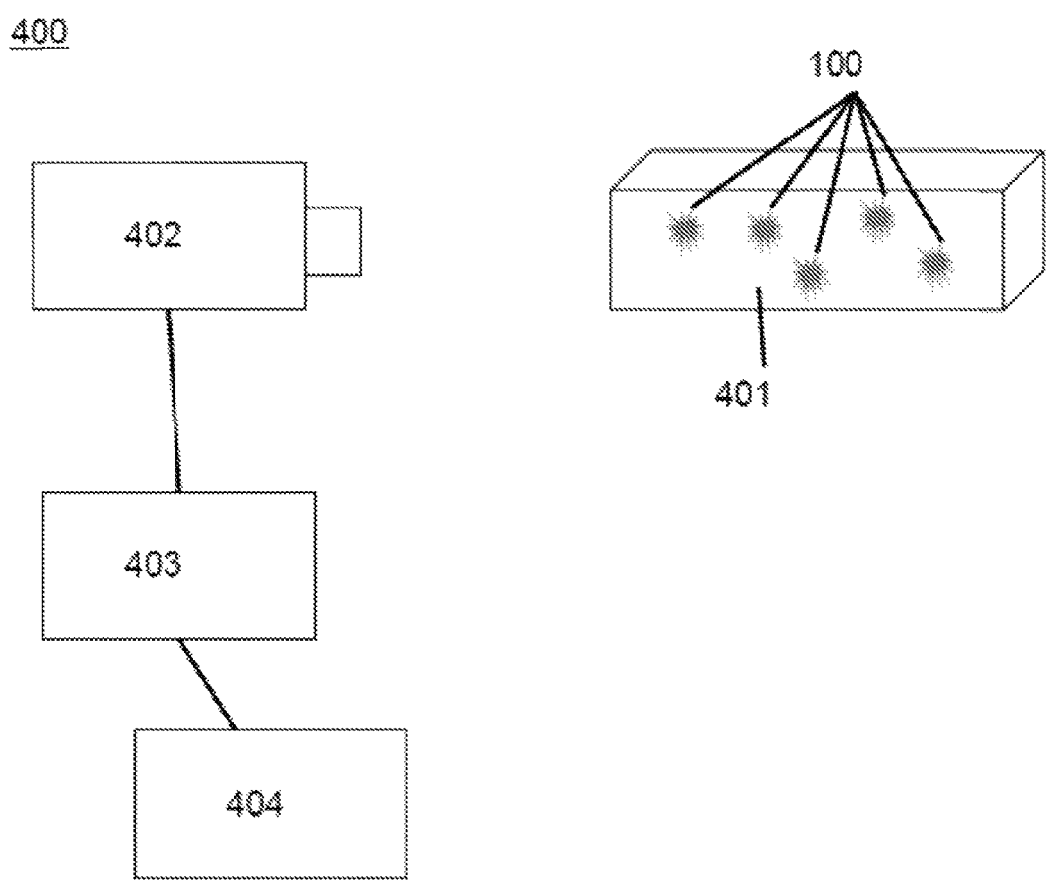
FIG. 4 is a schematic of a detector for determining information related to a substance that has been treated with coated mesoflowers that include a marker material.

FIG. 4 shows a detector 400 for determining information related to a substance 401. The substance 401 has been treated to include a plurality of coated mesoflowers 100 that include a marker material (for example, as described above with respect to FIG. 3). As described below, the mesoflowers 100 operate as "tags" that provide information associated with the substance 401.

The detector 400 includes a sensor 402 that detects a mesoflower enhanced optical property of the marker material (for example, an enhanced Raman spectrum) and generates optical property information indicative of the detected property. A processor 403 receives the optical property information from the sensor 402, and processes the optical property information to determine information related to a substance.

In some embodiments, the processor 403 is in communication with a storage device 404 that stores information indicative of an association between the detected optical property of the marker and information about the substance. For example, the storage device 404 may include a database associating the one or more features of the Raman spectra of various marker materials with corresponding information about the substance 401.

For example, in one embodiment, each of several possible markers may be associated with a particular production plant. All substances produced at a given plant are treated with coated mesoflowers including the marker corresponding to the plant and having a unique optical property. The database stored in storage device 404 may include a look up table that associates the unique optical properties with the corresponding plant. The processor 405 may access this look up table to identify the plant where the substance 401 was made based on the optical property information from the sensor 402.

Methods of Making Coated Mesoflowers

Figure 5:
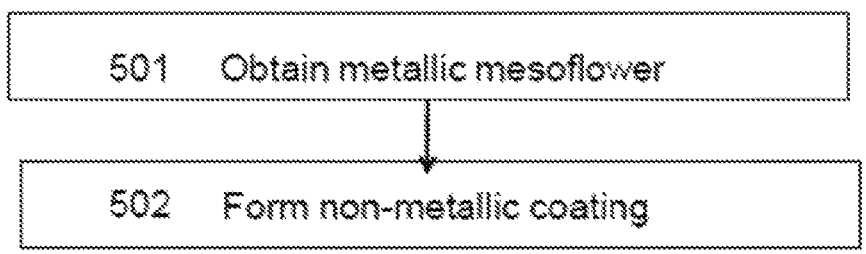
FIG. 5 is a flow diagram for a method of making a coated mesoflower.

FIG. 5 shows a method 500 of making a coated mesoflower 100 of the type described above. In step 501, a metallic mesoflower core is obtained. The metallic mesoflower cores may be produced using any suitable technique, for example, as described in the Examples below. As described above, the metallic mesoflower core may have a first surface, and includes at least one protrusion terminating in a tip.

In step 502, a non-metallic coating is formed covering and substantially conformal to the first surface, thereby creating an outer surface of the coated mesoflower. The coating be produced using any suitable technique, for example, using a sol-gel process as described in the Examples below.

In some embodiments, a marker material may be applied to the non-metallic coating. The marker material may have an optical property that is enhanced in the presence of the coated mesoflower. Applying the marker material may include at least partially embedding the marker material in the non-metallic coating. In some embodiments, the marker material does not contact the first surface of the metallic mesoflower core. The marker material may for example be physically and/or chemically adsorbed in the non-metallic coating.

In some embodiments, step 502 of forming the non-metallic coating includes forming a first layer including the marker material, and forming an overlayer covering the first layer. In some embodiments, the overlayer protects the marker material and/or inhibits removal of the marker material.

Some embodiments include various optional steps (not shown). For example, some embodiments include functionalizing the outer surface of the mesoflower with any suitable material including, for example, an organic chemical having a functional group. In various embodiments, the functionalization of the outer surface may be used to adjust a property of the mesoflower, for example the solubility of the mesoflower. For example, the functionalization may be chosen such that the mesoflower is hydrophobic, hydrophilic, or amphiphilic. In some embodiments, the functionalization of the outer surface may be used to attract a desired analyte, to target the mesoflower to a desired type of biological material, or for any other suitable purpose.

In some embodiments, step 502 of forming the non-metallic coating includes forming a cavity, channel, or other feature in the non-metallic coating, for example, using the techniques described in the Examples below. In some embodiments, the cavity includes a space formed between a tip of the metallic mesoflower core and the non-metallic coating. In some embodiments, the cavity, channel, or other features may be produced by applying heat to the coated mesoflower, or any other suitable technique.

For example, in some embodiments, molecules capped on the surface of the metallic mesoflower core 101 may act as template for the formation of pores in the non-metallic coating 104. For example, in some embodiments cetyl trimethyl ammonium bromide (CTAB) capped on the metallic mesoflower core 101 may act as template for the formation of mesoporous silica coating via base-catalyzed hydrolysis of TEOS and subsequent condensation of silica onto the metallic mesoflower core 101 surface, for example, using techniques of the type described in Gorelikov et al., Single-Step Coating of Mesoporous Silica on Cetyltrimethyl Ammonium Bromide-Capped Nanoparticles, *Nano Lett.*, 2008, 8, 369-373. The pore size of the mesoporous silica coating may be varied by controlling the reaction time.

In some embodiments, controlled etching of the non-metallic coating 104 may also assist the creation of pores. In some embodiments, etchant solutions such as ammonia saturated methanol (for example, as described in *Langmuir*, 2010, 26, 11784-11789) or sodium hydroxide (for example, as described in *Adv. Funct. Mater.*, 2010, 20, 2201-2214) may be used.

In some embodiments, a cavity, channel or other feature may be formed between the metallic mesoflower core 101 and the non-metallic coating 104 by etching the metallic mesoflower core 101 prior to application of the non-metallic coating 104. In various embodiments, any suitable etchant may be used. For example, in some embodiments, a gold mesoflower may be etched using aqua regia (a mixture of concentrated nitric acid and concentrated hydrochloric acid, in a volume ratio of 1:3). The size of the cavity, channel or other feature may be varied by controlling the reaction time.

In some embodiments, the cavities or channels may be filled with a substance, for example, a therapeutic substance such as a drug.

Coated Hollow Mesoflowers

As a variation to the coated mesoflowers as described above, coated hollow mesoflowers may be provided. A coated hollow mesoflower may include a hollow mesoflower core having a first surface and including at least one protrusion terminating in a tip, a non-metallic coating covering and substantially conformal to the first surface, thereby creating an outer surface of the coated hollow mesoflower, and a marker material having an optical property, and at least partially embedded in the non-metallic coating.

The hollow mesoflower core structure may have sizes and dimensions as described above for the metallic mesoflower core. The non-metallic coating may be as described above, and can for example include an oxide, such as a silicon oxide, a metal oxide, or combinations thereof. In some embodiments, the non-metallic coating has a thickness as described above, and can for example be about 2 nm to about 500 nm. The coated hollow mesoflowers may have characteristic morphologies as described above for the coated mesoflowers. In some embodiments, the non-metallic coating includes at least one cavity. The cavity, may in some embodiments, be a space formed between a tip of the hollow mesoflower core and the non-metallic coating. Methods of forming the cavity can be as described above.

In some embodiments, the optical property of the marker material is fluorescence. Suitable marker materials may include a fluorescent material. The fluorescent material may be invisible in visible light, and visible under ultraviolet light. In some embodiments, the fluorescent material includes organic molecules, for example, rhodamine 6G, fluorescein isothiocyanate, or any combination thereof. Other than organic molecules, the fluorescent material, may include the semiconductor quantum dot, rare-earth nanocrystal, metallic quantum cluster, or any combination thereof.

Methods of making the coated hollow mesoflowers and embedding the marker material may be as described above for the coated mesoflowers, but with an additional step of removing the metallic mesoflower core from the coated mesoflower, leaving behind the non-metallic coating which forms a shell covering the hollow mesoflower core structure. The removing step may include selectively etching the metallic mesoflower core with an acid. The etching can, for example, include etching by chemicals that will degrade the metal mesoflower core but not the non-metal coating covering the metal mesoflower core. The chemicals can, in some embodiments be an acid such as concentrated hydrochloric acid, concentrated nitric acid, or both. In some embodiments, the acid can be aqua regia (a mixture of concentrated nitric acid and concentrated hydrochloric acid, in a volume ratio of 1:3).

The coated hollow mesoflower can have high optical transparency to visible light, making it suitable for developing optically invisible tags in the forms of barcodes or other security codes. The unique structural attributes of the coated hollow mesoflower can provide an additional level of authentication to the tags. As described above, the coated hollow mesoflower can be labeled with a fluorescent material. The fluorescent labeled coated hollow mesoflower, when applied onto a substrate such as, but are not limited to, a glass substrate, a polymeric material, an optical fiber, cloth, paper or currency, is substantially invisible to the human eye under visible light, and even under a dark field microscope. Accordingly, in some embodiments, tags that include at least one coated hollow mesoflower is provided, wherein the optical property is substantially undetectable under a first condition and is detectable under a second condition different from the first condition. In some embodiments, the first condition is a first pH (for example, a substantially neutral pH), and the second condition is a second pH (for example, an acidic pH or an alkaline pH). In some embodiments, the first condition is a first temperature (for example, room temperature or cooler), and the second condition is a second temperature (for example, an elevated temperature resulting from application of heat). In some embodiments, the first condition is visible light, and the second condition is ultra-violet light. For example, when the tag is exposed to ultra-violet light under a fluorescent microscope, the fluorescent labeled coated hollow mesoflowers will become visible to the human eye.

An exemplary application of the coated hollow mesoflowers include detecting the presence of analytes. In some embodiments, detectors and methods for detecting an analyte are provided. The detector may include a plurality of the coated hollow mesoflowers as described herein, and a sensor configured to detect the optical property (for example, fluorescence) of the marker material in the presence of the analyte. In some embodiments, the method for detecting the analyte includes contacting the analyte with the plurality of the coated hollow mesoflowers as described herein, and detecting the optical property of the marker material in the presence of the analyte, for example, using the sensor. The optical property of the marker material can be greater in the presence of the coated hollow mesoflowers than in the absence of the coated hollow mesoflowers.

Another exemplary application of the coated hollow mesoflowers include delivering a therapeutic agent or a drug to a treatment area in a subject. The subject may be an animal or a human being. The coated hollow mesoflowers, in this application, includes at least one cavity, and one or both of the hollow mesoflower core and the cavity contain the therapeutic agent. In such applications, the coated hollow mesoflower, in some embodiments, may not require the marker material to be present in the non-metallic coating. In some embodiments, the method of delivering the therapeutic agent includes obtaining the plurality of coated hollow mesoflowers as described herein, and delivering the plurality of coated hollow mesoflowers to the treatment area. At least some or all of the coated mesoflowers can be configured to release the therapeutic agent, when delivered to the treatment area. For example, the coated hollow mesoflowers can be heated to release the therapeutic agent.

Due to its high optical transparency to visible light, the coated hollow mesoflower may have applications in anti-reflection coatings. In such applications, the coated hollow mesoflower, in some embodiments, may not require the marker material to be present in the non-metallic coating.

EXAMPLES

The following non-limiting examples are presented for illustrative purposes only.

Example 1

Synthesis of Gold Mesoflowers with $SiO_2$ Coating ($Au@SiO_2$)

In this example, gold mesoflowers were initially formed by the following process. A 20 mL volume of cetyl trimethyl ammonium bromide (CTAB) (at a concentration of 100 mM) was first heated to 80° C. in a round-bottom flask over a heating mantle. To this solution, 335 µL $Au^{3+}$ solution (at a concentration of 25 mM), 125 µL $AgNO_3$ solution (at a concentration of 10 mM), and 135 µL freshly prepared ascorbic acid solution (at a concentration of 100 mM) were added sequentially. Next, 1 mL of Au/oligoaniline nanoparticles was added immediately to this growth solution and the solution gently mixed. The resultant solution was kept undisturbed at 80° C. for 1 hour and allowed to cool to room temperature. After 1 hour, the solution was centrifuged at 4000 rpm for 5 minutes. The residue was washed with water three times, in order to remove excess CTAB. The slight yellowish residue of gold mesoflowers was redispersed in deionized water for further characterization. This procedure yielded mesoflowers with sizes of 1-2 µm. In other cases, the size of the mesoflowers can be tuned by changing the experimental parameters.

In some embodiments, the size of the metallic mesoflower can be controlled by controlling the amount of seed nanoparticles (for example, Au/oligoaniline nanoparticles) added during the growth process or by controlling the time of reaction (for example, as described in Nano Res., 2009, 2, 306-320). In general, the size of the mesoflower will increase with increased amounts of seed nanoparticles, increased reaction time, or combinations thereof.

Figure 6:
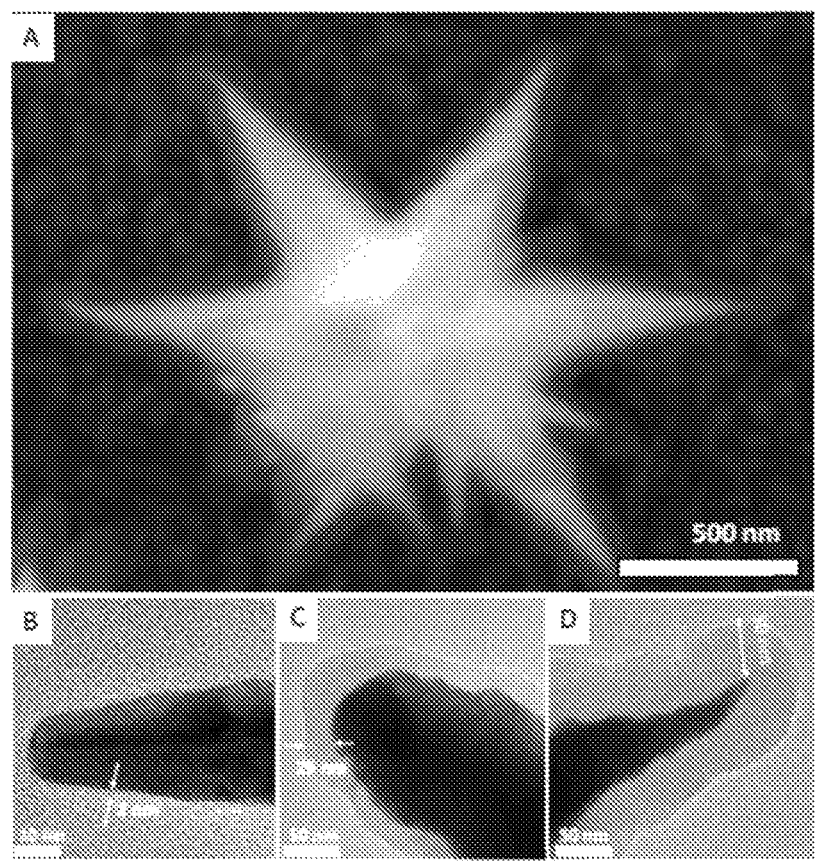
FIG. 6 shows electron microscope images of coated mesoflowers. Panel A shows a scanning electron microscope (SEM) image of a single Au@SiO$_2$ mesoflower. Panels B, C, and D, show transmission electron microscope (TEM) images of Au@SiO$_2$ mesoflowers with various coating thicknesses. Panel B shows a coating thickness of about 2 nm, panel C shows a coating thickness of about 25 nm, panel D shows a coating thickness of about 50 nm.

A silica ($SiO_2$) coating was formed over the gold mesoflowers, using a sol-gel process. In this process, 200 µL of Au mesoflowers was added to 20 mL of 2-propanol. Under continuous stirring, 1 mL of ammonia solution and 60 µL of tetraethyl orthosilicate (TEOS) were added. The reaction was allowed to proceed for 1 hour at room temperature under continuous stirring. The resultant solution was redispersed in water without adding any surfactant. The coated Au mesoflowers could be separated from the reaction medium by centrifuging at 4000 rpm and then redispersed in deionized water. The thickness of silica coating could be increased by increasing the amount of TEOS added, making it possible to tune the coating thickness from about 2 nm to about 500 nm. FIG. 6, panel A shows a scanning electron microscope (SEM) image of a single $Au@SiO_2$ mesoflower. FIG. 6 panels B, C, and D show transmission electron microscope (TEM) images of $Au@SiO_2$ mesoflowers with various coating thicknesses. Panel B shows a coating thickness of about 2 nm, panel C shows a coating thickness of about 25 nm, panel D shown a coating thickness of about 50 nm.

Example 2

Synthesis of Silver-Coated Gold Mesoflowers with $SiO_2$ Coating

In this example, gold mesoflowers were produced using substantially the same technique as described in EXAMPLE I. The gold mesoflowers were then coated with silver before coating the mesoflower in silica. As described below, in some cases this enhances the SERS activity.

The gold mesoflowers were coated with silver using the following process. The gold mesoflowers were redispersed in water. To this solution, 1 mL of $AgNO_3$ (at a concentration of 10 mM), and 200 µL of ascorbic acid solution (at a concentration of 100 mM) were added sequentially. This solution was kept at room temperature for 3 hours. After that, the solution was centrifuged at 3000 rpm for 5 minutes. Subsequently, the whitish-grey residue was redispersed in distilled water and again centrifuged.

The resulting silver coated gold mesoflowers were then coated with silica using the process described in EXAMPLE I. As in EXAMPLE I the thickness of silica coating could be conveniently increased by increasing the TEOS added, making it possible to tune the coating thickness from about 2 nm to about 500 nm.

Example 3

SERS Activity of Coated Mesoflowers with Crystal Violet as an Analyte

Figure 7:
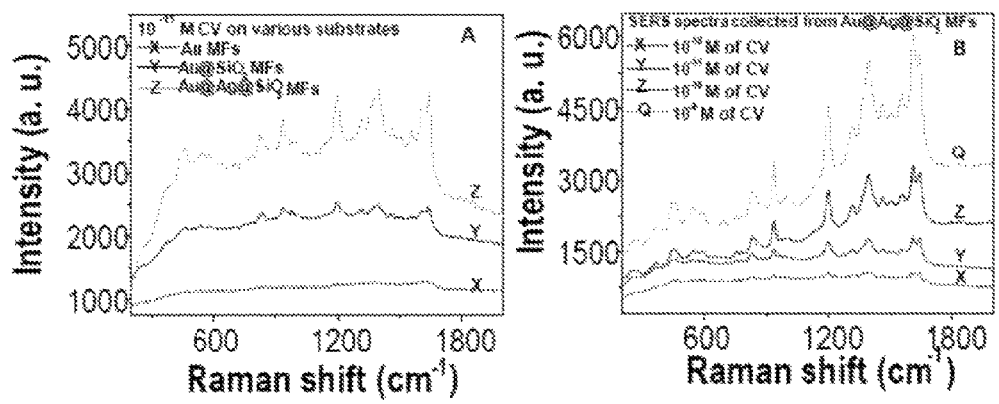
FIG. 7, panel A, shows SERS spectra of $10^{-11}$ M CV adsorbed on various types of mesoflowers. The spectrum for Au mesoflowers is marked with an "X", the spectra for Au@SiO$_2$ mesoflowers is marked with a "Y", and the spectra for Au@Ag@SiO$_2$ is marked with a "Z". Panel B, shows SERS spectra CV solutions at various concentrations adsorbed on Au@Ag@SiO$_2$ mesoflowers. The spectra for CV concentrations of $10^{-12}$, $10^{-11}$, $10^{-10}$, and $10^{-9}$ M are marked, respectively with the labels "X", "Y", "Z", and "Q".

In this example, Au@SiO$_2$ and Au@Ag@SiO$_2$ mesoflowers were formed using substantially the same techniques as described in EXAMPLE 1 and EXAMPLE 2. The SERS activity of various types of mesoflowers was tested by using crystal violet (CV) as an analyte. In order to compare the SERS activity, Raman spectra (taken across the UV, visible, and near infrared spectrum) were collected from uncoated Au mesoflowers, Au@SiO$_2$ mesoflowers, and Au@Ag@SiO$_2$ mesoflowers on which $10^{-11}$ M of CV molecules were adsorbed. The resulting spectra are shown in FIG. 7, panel A.

Both types of mesoflowers exhibit SERS enhancement of the Raman spectra of the CV, while the Raman signals due to the adsorbed CV molecules were too weak to be detectable in the uncoated Au mesoflowers.

The SERS enhancement was greater for Au@Ag@SiO$_2$ mesoflowers than for Au@SiO$_2$ mesoflowers across the measured range. These results clearly show the significant role of the SiO2 coating on SERS activity.

Raman spectra of CV solutions of various concentrations adsorbed on Au@Ag@SiO$_2$ mesoflowers were also obtained. The results are shown in FIG. 7, panel B. Even at a concentration as low as $10^{-12}$ M, the Raman features of adsorbed CV are visible in the measured data, which confirms the high SERS activity of Au@Ag@SiO$_2$ mesoflowers.

Example 4

Detection of DPA and DNT Using Coated Mesoflowers

In this example, Au@Ag@SiO$_2$ mesoflowers were used as a SERS substrate for the detection of various molecules including dipicolinic acid (DPA) and dinitrotoluene (DNT). DPA is a molecule that constitutes 5 to 15% of the dry weight of the bacterial spore of *Bacillus anthracis*, and so detection of the DPA molecule may be used in detecting such bacterial spores. DNT is an explosive surrogate, and so detection of the DNT molecule demonstrates a potential for use in explosive detection.

Au@Ag@SiO$_2$ mesoflowers were synthesized as described in EXAMPLE 2, and applied to a surface of a glass substrate. The surface with the Au@Ag@SiO$_2$ mesoflowers was drop casted with 20 μL of DPA (or DNT) solution. The substrate was then subjected to the SERS test in ambient air. The back-scattered light from the sample was collected using a 60× liquid immersion objective with an integration time of 1 second. The experiment was repeated for various concentrations of DPA (or DNT) adsorbed on the mesoflowers.

Figure 8:
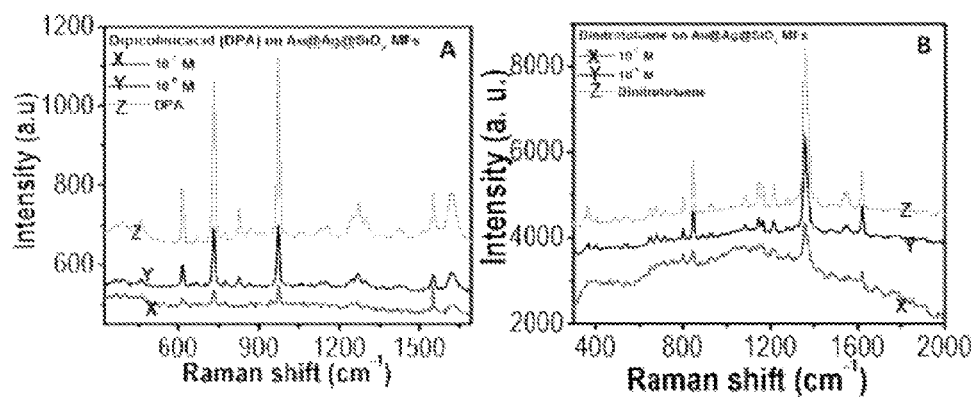
FIG. 8 shows SERS spectra collected from DPA solutions (panel A) and DNT solutions (panel B) having various concentrations adsorbed on Au@Ag@SiO$_2$ mesoflowers. In each panel, a SERS spectrum for DPA/DNT (panel A/panel B) solution without mesoflowers is shown for comparison. In panel A, spectra for DPA concentrations of $10^{-7}$, and $10^{-8}$ M adsorbed on Au@Ag@SiO$_2$ mesoflowers are marked, respectively with the labels "X" and "Y". The Raman spectra for DPA is shown for comparison and labeled "Z". In panel B, spectra for DNT concentrations of $10^{-7}$, and $10^{-6}$ M adsorbed on Au@Ag@SiO$_2$ mesoflowers are marked, respectively with the labels "X" and "Y". The Raman spectra for DNT is shown for comparison and labeled "Z".

The results are shown in FIG. 8, panel A (for DPA) and FIG. 8, panel B (for DNT). The characteristic Raman features of DPA and DNT molecules could be detected at concentrations as low as $10^{-8}$ and $10^{-7}$ M, respectively. For both DPA and DNT, the resulting Raman features were comparable with the standard solid samples. The enhancement factors were calculated in both the cases and were found to be of the order of $\sim 10^7$ and $\sim 10^8$ for DNT and DPA, respectively.

Example 5

Detection of Explosive Molecules Using Coated Mesoflowers

In this example, coated mesoflowers were used to detect explosive molecules at the nanogram level. Au@SiO$_2$ mesoflowers were synthesized as described in EXAMPLE 1. A powder of the mesoflowers was applied to a glass substrate. A 10 μl volume of a solution of trinitrotoluene (TNT) was drop-casted onto the glass substrate and dried. The process was repeated for various concentration of TNT. Raman spectra of the sample slides were collected.

Figure 9:
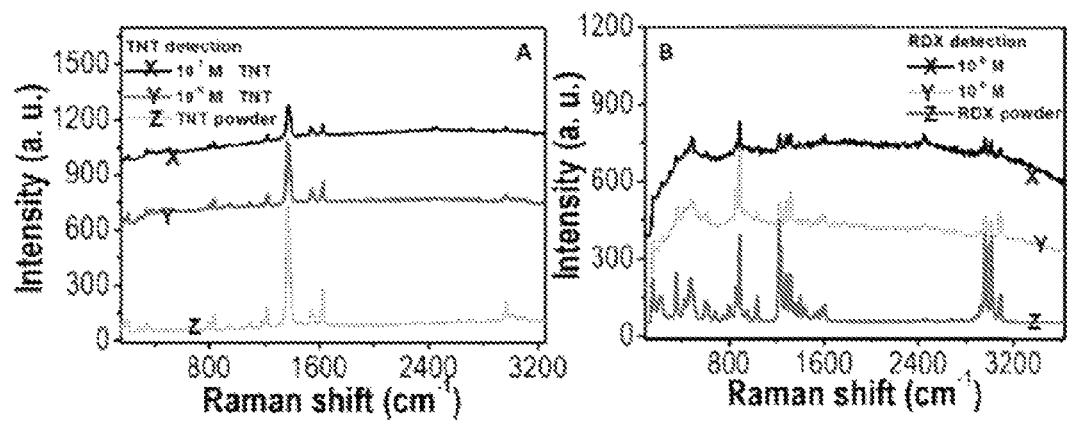
FIG. 9 shows SERS spectra collected from TNT (panel A) and RDX (panel B) having various concentrations adsorbed on a powder of Au@SiO$_2$ mesoflowers. In each panel, a SERS spectrum for TNT/RDX (panel A/panel B) powder without mesoflowers is shown for comparison. In panel A, spectra for TNT concentrations of $10^{-7}$, and $10^{-6}$ M adsorbed on Au@Ag@SiO$_2$ mesoflowers are marked, respectively with the labels "X" and "Y". The Raman spectra for TNT powder is shown for comparison and labeled "Z". In panel B, spectra for RDX concentrations of $10^{-6}$, and $10^{-5}$ M adsorbed on Au@Ag@SiO$_2$ mesoflowers are marked, respectively with the labels "X" and "Y". The Raman spectra for RDX powder is shown for comparison and labeled "Z".

The results are shown in FIG. 9, panel A. For spectra collected for TNT adsorbed at concentrations as low as $10^{-7}$ M, the characteristic Raman spectra features of TNT were detectable. The detected features were comparable with the Raman features of TNT powder in the absence of mesoflowers.

Similarly, a powder of Au@SiO$_2$ mesoflowers was applied to a glass substrate. A 10 μl volume of a solution of cyclotrimethylenetrinitramine (RDX) was drop-casted onto the glass substrate and dried. The process was repeated for various concentration of RDX. Raman spectra of the sample slides were collected. The results are shown in FIG. 9, panel B. For spectra collected for RDX adsorbed at concentrations as low as $10^{-6}$ M, the characteristic Raman spectra features of RDX were detectable. The detected features were comparable with the Raman features of RDX powder in the absence of mesoflowers.

Example 6

Enhanced Thermal Stability of Coated Mesoflowers

Coated mesoflowers can exhibit enhanced thermal stability relative to their bare counterparts. In this example, Au@SiO$_2$ mesoflowers having a shell thickness of 50 were formed using the techniques described in EXAMPLE 2. Bare Au mesoflowers were also formed as a control.

Figure 10:
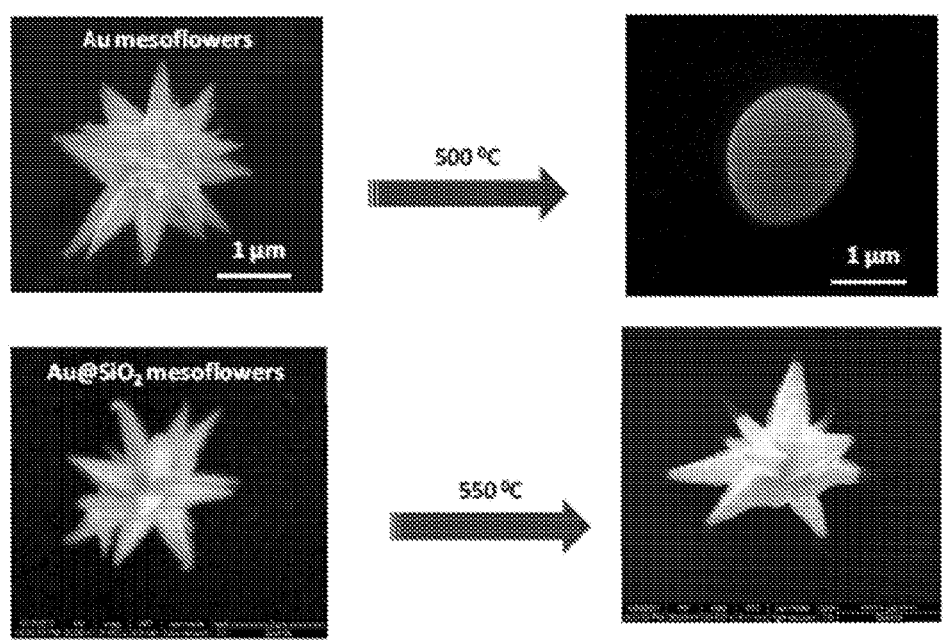
FIG. 10 shows SEM images of Au and Au@SiO$_2$ mesoflowers treated at high temperatures. The top left panel shows a bare Au mesoflower prior to heat treatment. The top right panel shows the bare Au mesoflower after heat treatment at 500 degrees C. The bottom left panel shows an Au@SiO$_2$ mesoflower prior to heat treatment. The bottom right panel shows the Au@SiO$_2$ mesoflower after heat treatment at 550 degrees C.

Both types of mesoflowers were exposed to elevated temperatures. SEM images of the mesoflowers were taken before and after this heat treatment. Exemplary results are shown in FIG. 10. As shown in FIG. 10, the structure of the bare Au mesoflower was destroyed by the heat treatment at 500 degrees C., while the structure of the coated Au@SiO$_2$ mesoflower remained stable at a temperature of 550 degrees C. Repeating the process for various treatment temperatures, coated Au@SiO$_2$ mesoflowers were found to be stable at temperatures up to 675 degrees C. In contrast, bare Au mesoflowers were found to lose stability at temperatures above 350 degrees C.

It is expected that further increasing the thickness of the silica coating may further enhance the thermal stability of the mesoflowers.

The enhanced thermal stability of the coated mesoflowers makes them suitable for various high temperature applications, for example, in sensors that can be used at high temperature environments.

Similarly, in some embodiments, non-metallic coated mesoflowers (for example, silica-coated mesoflowers) are expected to be stable even in acidic environments (for example, having a pH less than 7.0, less than 6.0, less than 5.0, less than 4.0. less than 3.0, less than 2.0, or less than 1.0, for example, in the range of 0.0-7.0, or any subrange thereof).

Example 7

Synthesis of Smart Barcode Materials Using Coated Mesoflowers

Figure 11:
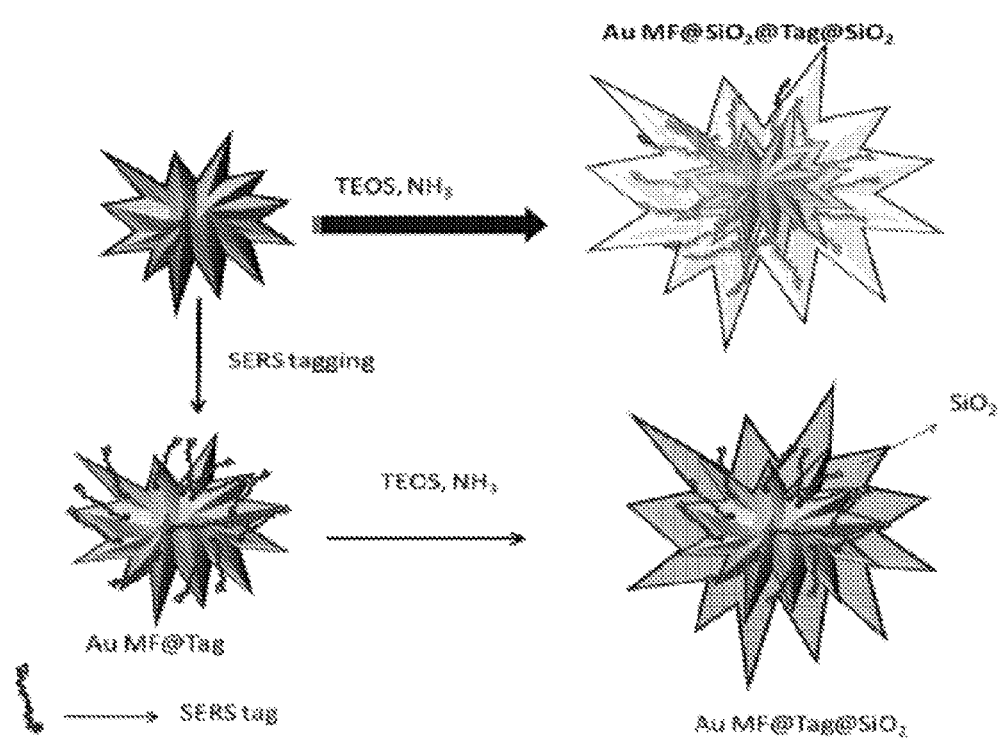
FIG. 11 shows a pictorial representation of SERS based silica-coated smart barcode mesoflowers.

In this example, two types of smart barcode materials are made using silica-coated mesoflowers. FIG. 11 shows a pictorial illustration of the synthesis of both types of smart barcode materials.

Metallic mesoflower cores (for example bare Au or Au@Ag mesoflowers) are synthesized, for example, using the techniques described in EXAMPLE 1 or EXAMPLE 2 (FIG. 11, top left). A marker material such as a SERS active tag molecule (for example crystal violet) is then adsorbed onto the metallic mesoflower core, using any suitable technique (FIG. 11, bottom left). A silica overlayer is then applied, for example, using the techniques described in EXAMPLE 1 or EXAMPLE 2 (FIG. 11, bottom right). This overlayer prevents the adsorbed tag molecules from being liberated from the mesoflower.

For the second type of smart barcode material, coated metallic mesoflower cores (for example Au@SiO$_2$ or Au@Ag@SiO$_2$ mesoflowers) are synthesized, for example, using the techniques described in EXAMPLE 1 or EXAMPLE 2. A selected type of marker material such as SERS active tag molecules (for example crystal violet) is then adsorbed onto the outer surface of the coated mesoflowers, using any suitable technique. The coating on the mesoflower cores physically separates the tag molecules from the core metallic mesoflowers. A non-metallic overlayer (for example a silica overlayer) is then applied to the tagged coated mesoflower (FIG. 11, top right), for example, using the coating techniques described in EXAMPLE 1 and EXAMPLE 2. In some case, the first silica coating will amplify the SERS activity. The overlayer protects the tag molecules from their surroundings. The silica coating makes the mesoflower a corrosion resistant material, which can withstand extreme acidic environments and temperature (for example, as described in EXAMPLE 6).

Example 8

Smart Barcodes Using Coated Mesoflowers for Material Identification

Figure 12:
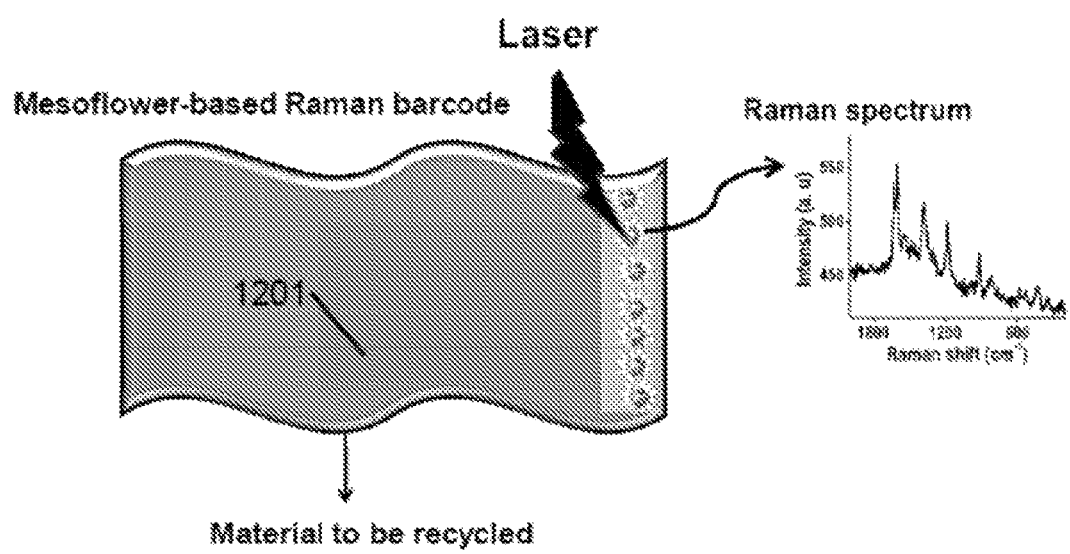
FIG. 12 shows a pictorial representation of a mesoflower-based Raman barcode used for recycling a material.

Referring to FIG. 12, in this example, coated mesoflowers tagged with a selected marker material or tag material (for example, a Raman active material or a fluorescent material) are introduced to a material 1201. In some cases, the tagged mesoflowers may be formed using the techniques described in EXAMPLE 7. For example, different types of materials 1201 can be treated with mesoflowers tagged with a material having a corresponding distinct optical property (for example, a selected Raman spectrum or selected fluorescence properties).

In various embodiments, the material 1201 may be any suitable material, for example, fibers, cloths, papers, or currencies. In some cases, mesoflowers with sharp stems can penetrate into the material 1201. Once attached, the stems act as hooks that may prevent detachment from the material 1201, for example, by mechanical agitation or washing.

The material 1201 may be identified based on a measured optical property of the tag material. As shown, a laser Raman spectroscopy set up is used to acquire a Raman spectrum (inset right) for the tagged mesoflowers attached to the material 1201. The spectrum is then used to identify the material, for example, to sort the material for recycling.

In other embodiments, a similar approach may be used for a variety of other applications including, for example, validating the authenticity of a material (for example, a currency) or identifying the production source of a material.

Example 9

Coated Mesoflowers for Medical Applications

In this example, coated mesoflowers, for example, of the type describe in the EXAMPLES above, are introduced into a human or animal subject. The coating on the mesoflowers (for example, a silica coating) can be biocompatible. Sharp protrusions of the mesoflowers can easily penetrate to the body of the subject. Mesoflowers with channels at the tip of each stem, loaded with the drugs, can be used for drug release (for example, painless release). The coating may also be functionalized with various suitable molecules, for example, to target the mesoflowers to certain types of biological tissue (for example, tumor tissue or cancer cells).

As described herein, the coated mesoflowers may selectively absorb light in a desired wavelength range. For example, coated mesoflowers may absorb light in the near infrared and infrared. This absorption property is useful for many bio-related applications. For example, the mesoflowers may be introduced to a subject, for example, to target a desired type of tissue. Light in the near infrared and infrared can be applied to the subject. Local heating generated by the mesoflowers by absorption of the light can be used, for example, can be used, for example, to destroy tumors or cancer cells.

Example 10

Smart Barcodes Using Coated Hollow Mesoflowers for Material Identification

Gold mesoflower cores with silica coatings (Au@SiO$_2$) were used as templates for making hollow SiO$_2$ mesoflowers. The Au@SiO$_2$ was formed using the techniques described in EXAMPLE 1. Selective etching of the gold mesoflower core was carried out using aqua-regia (a mixture of concentrated nitric acid and concentrated hydrochloric acid, in a volume ratio of 1:3) to form the hollow SiO$_2$ mesoflowers. The hollow SiO$_2$ mesoflowers were labeled with a UV-visible ink (rhodamine 6G) by allowing the ink to adsorb onto the silica surface.

The labeled hollow silica mesoflowers can be applied onto a material such as a glass substrate, an optical fiber or a polymeric material. When applied to the material, the labeled hollow silica mesoflowers is substantially invisible under visible light and under a dark field microscope.

The material may be identified by exposing the material to UV light which will cause the labeled hollow silica mesoflowers to become visible.

The subject matter described herein sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," and so on). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

Furthermore, in those instances where a convention analogous to "at least one of A, B, and C, and so on" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, and so on). In those instances where a convention analogous to "at least one of A, B, or C, and so on" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, and so on).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A coated mesoflower comprising:
   a metallic mesoflower core that includes a first surface, wherein the metallic mesoflower core includes at least one protrusion terminating in a tip;
   a non-metallic coating that covers and is substantially conformal to the first surface such that the non-metallic coating creates an outer surface of the coated mesoflower and comprises at least one cavity, wherein the cavity comprises a space formed between the tip of the metallic mesoflower core and the non-metallic coating; and
   a marker material having an optical property that is enhanced in the presence of the coated mesoflower.

2. The coated mesoflower of claim 1, wherein the marker material is a Raman active material, a fluorescent material, or both.

3. The coated mesoflower of claim 2, wherein the Raman active material comprises surface enhanced Raman scattering (SERS) active molecules.

4. The coated mesoflower of claim 2, wherein the Raman active material comprises crystal violet, rhodamine 6G, methylene blue, or any combination thereof.

5. The coated mesoflower of claim 2, wherein the fluorescent material comprises organic molecules, a semiconductor quantum dot, a rare-earth nanocrystal, a metallic quantum cluster, or any combination thereof.

6. The coated mesoflower of claim 5, wherein the organic molecules comprise rhodamine 6G, fluorescein isothiocyanate, or any combination thereof.

7. The coated mesoflower of claim 1, wherein the marker material is at least partially embedded in the non-metallic coating.

8. The coated mesoflower of claim 1, wherein the marker material does not contact the first surface of the metallic mesoflower core.

9. The coated mesoflower of claim 1, wherein the non-metallic coating comprises:
   a first layer comprising the marker material; and
   an overlayer that covers the first layer.

10. The coated mesoflower of claim 1, wherein the non-metallic coating comprises at least one oxide.

11. The coated mesoflower of claim 1, wherein the non-metallic coating comprises silicon oxide, a metal oxide, or combinations thereof.

12. The coated mesoflower of claim 1, wherein the metallic mesoflower core comprises Au, Ag, or both Au and Ag.

13. The coated mesoflower of claim 1, wherein the metallic mesoflower core comprises:
a core of a first metallic material; and
a shell of a second metallic material different from the first metallic material.

14. The coated mesoflower of claim 1, wherein the non-metallic coating has a thickness of about 2 nm to about 500 nm.

15. A method of making a coated mesoflower comprising:
forming a protrusion on a metallic mesoflower core having a first surface, wherein the protrusion terminates in a tip;
covering the first surface with a non-metallic coating that is substantially conformal to the first surface, thereby creating an outer surface of the coated mesoflower;
forming a cavity in the non-metallic coating, wherein forming the cavity comprises forming a space between the tip of the metallic mesoflower core and the non-metallic coating; and
applying a marker material to the non-metallic coating, the marker material having an optical property that is enhanced in the presence of the coated mesoflower.

16. The method of claim 15, wherein applying the marker material to the non-metallic coating comprises at least partially embedding the marker material in the non-metallic coating, and wherein the marker material does not contact the first surface of the metallic mesoflower core.

17. The method of claim 15, wherein the covering comprises:
forming a first layer comprising the marker material; and
forming an overlayer covering the first layer.

18. The method of claim 15, further comprising functionalizing the outer surface of the coated mesoflower.

\* \* \* \* \*

UNITED STATES PATENT AND TRADEMARK OFFICE
CERTIFICATE OF CORRECTION

PATENT NO. : 9,903,821 B2
APPLICATION NO. : 14/888193
DATED : February 27, 2018
INVENTOR(S) : Thalappil et al.

Page 1 of 1

It is certified that error appears in the above-identified patent and that said Letters Patent is hereby corrected as shown below:

In the Specification

Column 1, Line 10, delete "filed Apr. 30, 2014," and insert -- filed on Apr. 30, 2014, --, therefor.

Column 1, Line 12, delete "filed May 1, 2013," and insert -- filed on May 1, 2013, --, therefor.

Column 1, Line 16, delete "entirety." and insert -- entireties. --, therefor.

Column 1, Line 47, delete "scattering,also know" and insert -- scattering, also known --, therefor.

Column 7, Line 22, delete "non-metallic coating 101." and insert -- non-metallic coating 104. --, therefor.

Column 8, Line 54, delete "detector 100 may" and insert -- detector may --, therefor.

Column 9, Line 1, delete "monochrometer," and insert -- monochromator, --, therefor.

Column 19, Line 33, delete "recitation no" and insert -- recitation, no --, therefor.

Column 19, Line 56, delete "general such" and insert -- general, such --, therefor.

Column 19, Line 63, delete "general such" and insert -- general, such --, therefor.

Signed and Sealed this
Nineteenth Day of June, 2018

Andrei Iancu
*Director of the United States Patent and Trademark Office*